United States Patent
Ollivier

(12)
(10) Patent No.: US 6,252,065 B1
(45) Date of Patent: *Jun. 26, 2001

(54) PROCESS FOR THE PREPARATION OF LACTAMS FROM THE CORRESPONDING CYCLOALKANONE OXIMES

(75) Inventor: Jean Ollivier, Arudy (FR)

(73) Assignee: Elf Atochem, S.A. (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/400,994

(22) Filed: Sep. 21, 1999

(30) Foreign Application Priority Data

Sep. 21, 1998 (FR) .................................................. 98 11733

(51) Int. Cl.⁷ ...................... C07D 225/02; C07D 201/04
(52) U.S. Cl. ........................... 540/464; 540/535; 540/536
(58) Field of Search ..................................... 540/464, 535, 540/536

(56) References Cited

U.S. PATENT DOCUMENTS

| | | | |
|---|---|---|---|
| 2,721,199 | 10/1955 | Huber | 260/239.3 |
| 4,211,700 | * 7/1980 | Michel et al. | 260/239.3 |
| 4,689,412 | * 8/1987 | Rademacher et al. | 540/464 |

FOREIGN PATENT DOCUMENTS 2 417 501    9/1979   (FR) .

* cited by examiner

*Primary Examiner*—Bruck Kifle
(74) *Attorney, Agent, or Firm*—Millen, White, Zelano & Branigan, P.C.

(57) ABSTRACT

For the preparation of lactams comprising 6 to 12 carbon atoms from the corresponding cycloalkanone oximes by rearrangement according to the Beckmann reaction in the presence of acid, the process is characterized in that use is made of methanesulphonic acid.

21 Claims, No Drawings

PROCESS FOR THE PREPARATION OF LACTAMS FROM THE CORRESPONDING CYCLOALKANONE OXIMES

CROSS-REFERENCE TO RELATED APPLICATION

This application is related to a concurrently filed and commonly owned application entitled "Process for the Preparation of Lauryllactam by Photonitrosation of Cyclododecane and Beckmann Rearrangement in the Presence of Methanesulphonic Acid", by Ollivier et al., based on French application 98/11734 filed on Sep. 21, 1998, respectively.

FIELD OF THE INVENTION

The present invention relates to the preparation of lactams which are used as base monomers for polyamides. More specifically, it relates to a process for the preparation of lactams from the corresponding cycloalkanone oximes by rearrangement according to the Beckman reaction, in which process methanesulphonic acid is used.

BACKGROUND OF THE INVENTION

The Beckmann rearrangement reaction, which consists in converting ketoximes to the corresponding substituted amides by means of acidic reagents, has been known for a very long time.

This reaction is taken advantage of in the industrial production of lactams from cyclic ketoximes, more particularly in order to form caprolactam and lauryllactam, which are base monomers of polyamide-6 and polyamide-12 respectively.

Provision has been made for the use of various acidic reagents in carrying out the Beckmann rearrangement.

The use of sulphuric acid, alone (see DE-8-15 45 653 and FR-A-2 417 501) or as a mixture with trifluoroacetic acid (see JP-A-51034185) or sulphur trioxide and chlorosulphonic acid (see JP-A-57031660).

Provision has been made for the use of phosphoric acid (see CH-A-530402 and JP-A-62149665) or polyphosphoric acid (see DE-B-1 545 617).

The use has also been disclosed of acetic acid (see CH-A-394212), of a mixture of acetic acid and cyanuric acid (see JP-B-71023740), of a mixture of acetic acid and acetone (see JP-A-51004163), of a mixture of acetic acid, acetone and a fluorinated catalyst (see JP-A-51004164) and of a mixture of acetic acid or acetic anhydride and hydrofluoric acid (see U.S. Pat. No. 3,609,142).

Finally, provision has been made for the use of hydrochloric acid in conjunction with a polar organic solvent (see DE-A-1620478) or with a catalyst, for example a-metal salt (see U.S. Pat. No. 3,904,608) or a mixture of silica and alumina.

Sulphuric acid is by far the most commonly employed acid on an industrial scale. However, sulphuric acid is not without disadvantages.

It is known that, under the temperature conditions of the rearrangement (greater than 135° C.), sulphuric acid is a factor which promotes the appearance of hydrolysis side reactions. This hydrolysis takes place on the starting cycloalkanone oxime, which it converts to ketone, on the one hand, and on the final lactam, which it converts to amino acid, on the other hand. This results in a decrease in the production of lactam and additional difficulties in the subsequent stages of separation and purification of the lactam.

When the oxime to be treated comprises a residual chlorinated solvent originating from the preceding stage, as is in particular the case when photonitrosation of cycloalkane is involved, two side reactions appear.

The first reaction leads to partial decomposition of the sulphuric acid with release of sulphur dioxide. During the various operations of recycling the organic phase comprising the unreacted cycloalkane, the content of sulphur dioxide increases, the effect of which is to slow down the photonitrosation reaction.

The second side reaction causes decomposition of the residual chlorinated solvent to phosgene, which is toxic to man.

Finally, all the effluents comprising sulphuric acid which are generated by the industrial process can only be recycled at the price of a lengthy, difficult and expensive treatment.

SUMMARY OF THE INVENTION

It has now been found that the abovementioned disadvantages can be mitigated and thus that it is possible to contribute to improving the profitability of the industrial plant by replacing sulphuric acid with methanesulphonic acid.

The subject-matter of the invention is therefore a novel process for the preparation of lactams comprising 6 to 12 carbon atoms from the corresponding cycloalkanone oximes by rearrangement according to the Beckmann reaction, this process being characterized in that the acid employed is methanesulphonic acid.

The Beckmann rearrangement is generally carried out in a reactor operating under hot conditions and with vigorous stirring.

The cycloalkanone oxime is generally introduced into the reactor in the form of a solution comprising 10 to 40% by weight of oxime, preferably 25 to 35%, in methanesulphonic acid.

For obvious reasons of safety related to the very high exothermicity of the reaction, it is preferable to introduce the oxime solution into a reactor which comprises an appropriate volume of methanesulphonic acid maintained at the temperature required for carrying out the rearrangement. This volume can, as is known to a person skilled in the art, vary within a wide range according to whether the reaction is carried out continuously or batchwise.

The strength by weight of the methanesulphonic acid is generally between 70 and 90%, preferably 95 and 99%.

The reaction is generally carried out at a temperature of between 120 and 180° C., preferably 140 and 160° C., and for a period of time such that the residence time in the reactor varies from 2 minutes to 1 hour, preferably 15 to 30 minutes.

The rearrangement is carried out with vigorous stirring. In the present invention, the expression "vigorous stirring" is understood to mean stirring which exhibits a Reynolds number (Re) of greater than 10,000, calculated according to the formula:

$$Re = l^2 n \rho / \mu$$

in which l is the diameter of the stirring component n is the number of revolutions per second $\rho$ is the density of the reaction mixture $\mu$ is the viscosity of the reaction mixture.

On conclusion of the reaction, the lactam is recovered in the methanesulphonic acid. This solution is generally subjected to one or more separation and purification stages well known to a person skilled in the art. The recovered methanesulphonic acid can easily be purified, for example by simple distillation, in order to be able to recycle it in the process.

The examples which follow make it possible to illustrate the invention.

EXAMPLE 1

231 g of a solution comprising 31% by weight of cyclododecanone oxime (0.363 mol) in methanesulphonic acid are added over 1 hour to 100 g of 90% by weight methanesulphonic acid, which acid is maintained at 120° C. with stirring (Re>10,000). The reaction mixture is brought to 135–140° C. for 1 hour in order to bring the rearrangement to completion.

At the end of the reaction, 70.9 g of lauryllactam are recovered (yield: 99%). No trace of amino acid resulting from the hydrolysis of lauryllactam is found.

EXAMPLE 2 (COMPARATIVE)

250 g of a solution comprising 30% by weight of cyclododecanone oxime (0.38 mol) in sulphuric acid are added over one hour to 100 g of 98% by weight sulphuric acid, which acid is maintained at 120° C. with stirring (Re>10,000).

After reacting for 1 hour at 135–140° C., 73.12 g of lauryllactam are recovered (yield: 97.5%).

In addition, the reaction mixture comprises 1.125 g of cyclododecanone and 0.75 g of 12-aminododecanoic acid.

1.44 g of sulphur dioxide are produced. The rearrangement gases comprise phosgene.

EXAMPLE 3

225 g of a solution comprising 35% by weight of cyclohexanone oxime (0.697 mol) in methanesulphonic acid are added over 1 hour to 100 g of 90% by weight methanesulphonic acid, which acid is maintained at 120° C. with stirring (Re>10,000). The reaction mixture is brought to 135–140° C. for 1 hour in order to bring the rearrangement to completion.

At the end of the reaction, 77.96 g of caprolactam are recovered (yield: 99%). No trace of amino acid resulting from hydrolysis of the caprolactam is found.

EXAMPLE 4 (COMPARATIVE)

228 g of a solution comprising 35% by weight of cyclohexanone oxime (0.706 mol) in sulphuric acid are added over one hour to 100 g of 98% by weight sulphuric acid, which acid is maintained at 120° C. with stirring (Re>10,000).

After reacting for 1 hour at 135–140° C., 78.2 g of caprolactam are recovered (yield: 98%).

In addition, the reaction mixture comprises 1.125 g of cyclododecanone and 0.75 g of 12-aminododecanoic acid.

1.4 g of sulphur dioxide are produced. The rearrangement gases comprise 20 ppm of phosgene.

Whereas the acid employed is advantageously methanesulphonic acid, it is also contemplated that the methanesulphonic acid may be mixed with other acids so long as the net effect is not to lose all the beneficial effects associated with the use of methanesulphonic acid.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 98/11733, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the preparation of lactams comprising 6 to 12 carbon atoms from the corresponding cycloalkanone oximes by rearrangement according to the Beckmann reaction in the presence of acid, the improvement wherein said acid comprises methanesulphonic acid.

2. A process according to claim 1, wherein the cycloalkanone oxime is in the form of a solution comprising 10 to 40% by weight of oxime in methanesulphonic acid.

3. A process according to claim 2, wherein the solution comprises 25 to 35% by weight of oxime.

4. A process according to claim 1, wherein the methanesulphonic acid is of a strength by weight of between 70 and 90%.

5. A process according to claim 1, wherein the reaction is carried out at a temperature of between 120 and 180° C.

6. A process according to claim 1, wherein the reaction is carried out with stirring which exhibits a Reynolds number of greater than 10,000.

7. A process according to claim 3, the methanesulphonic acid is of a strength by weight of between 70 and 90%.

8. A process according to claim 2, wherein the reaction is carried out at a temperature of between 120 and 180° C.

9. A process according to claim 2, wherein the reaction is carried out with stirring which exhibits a Reynolds number of greater than 10,000.

10. A process according to claim 5, wherein the reaction is carried out with stirring which exhibits a Reynolds number of greater than 10,000.

11. A process according to claim 1, for preparing lauryllactam.

12. A process according to claim 1, for preparing caprolactam.

13. A process according to claim 8, for preparing lauryllactam.

14. A process according to claim 9, for preparing lauryllactam.

15. A process according to claim 10, for preparing lauryllactam.

16. A process according to claim 1, wherein the methanesulphonic acid is of a strength by weight of between 95 and 99%.

17. A process according claim 1, wherein the reaction is carried out at a temperature of between 140 and 160° C.

18. A process according to claim 1, wherein the residence time is from 2–60 minutes.

19. A process according to claim 1, wherein the residence time is from 15–30 minutes.

20. In a process for the preparation of lactams comprising 6 to 12 carbon atoms from the corresponding cycloalkanone oximes by rearrangement according to the Beckman reaction in the presence of acid, the improvement wherein said acid consists essentially of methanesulphonic acid.

21. A process according to claim 1, free of sulfuric acid.

* * * * *

(12) EX PARTE REEXAMINATION CERTIFICATE (5726th)
United States Patent
Ollivier

(10) Number: US 6,252,065 C1
(45) Certificate Issued: *Mar. 27, 2007

(54) PROCESS FOR THE PREPARATION OF LACTAMS FROM THE CORRESPONDING CYCLOALKANONE OXIMES

(75) Inventor: Jean Ollivier, Arudy (FR)

(73) Assignee: Elf Atochem, S.A., Paris-Defense (FR)

Reexamination Request:
No. 90/006,534, Feb. 3, 2003

Reexamination Certificate for:
Patent No.: 6,252,065
Issued: Jun. 26, 2001
Appl. No.: 09/400,994
Filed: Sep. 21, 1999

(*) Notice: This patent is subject to a terminal disclaimer.

(30) Foreign Application Priority Data

Sep. 21, 1998 (FR) .......................................... 98 11733

(51) Int. Cl.
*C07D 225/02* (2006.01)
*C07D 201/04* (2006.01)

(52) U.S. Cl. ..................... 540/464; 540/535; 540/536
(58) Field of Classification Search .............. 540/464, 540/535, 536
See application file for complete search history.

(56) References Cited

FOREIGN PATENT DOCUMENTS

JP 05-051366 A 3/1993

OTHER PUBLICATIONS

Full YTH translation of JP 05–051336.
Abstracts of Japan of JP 05–051366, and partial translations (Koshiba & Partners translation and JPO machine translation).

*Primary Examiner*—Richard Raymond

(57) ABSTRACT

For the preparation of lactams comprising 6 to 12 carbon atoms from the corresponding cycloalkanone oximes by rearrangement according to the Beckmann reaction in the presence of acid, the process is characterized in that use is made of methanesulphonic acid.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 20 is confirmed.

Claims 1–19 are cancelled.

Claim 21 is determined to be patentable as amended.

New claims 22–25 are added and determined to be patentable.

21. [A process according to claim 1] *In a process for the preparation of lactams comprising 6 to 12 carbon atoms from the corresponding cycloalkanone oximes by rearrangement according to the Beckmann reaction in the presence of acid, the improvement wherein said acid consists essentially of methanesulfonic acid and the cycloalkanone oxime is in the form of a solution comprising 10 to 40% by weight of oxime in methanesulfonic acid,* free of sulfuric acid.

22. *A process for the preparation of lactams comprising 6 to 12 carbon atoms from the corresponding cycloalkanone oximes by rearrangement according to the Beckmann reaction in the prescence of acid, comprising introducing a solution consisting essentially of methanesulphonic acid and a cycloalkanone oxime.*

23. *A process according to claim 22, wherein the lactam is lauryl lactam.*

24. *A process for the preparation of lactams comprising 6 to 12 carbon atoms from the corresponding cycloalkanone oximes by rearrangement according to the Beckmann reaction in the prescence of acid, comprising introducing a solution consisting of methanesulphonic acid and a cycloalkanone oxime.*

25. *A process according to claim 24, wherein the lactam is lauryl lactam.*

* * * * *